United States Patent [19]

Khan et al.

[11] 4,117,224

[45] Sep. 26, 1978

[54] PREPARATION OF SUCROSE 6,6'-DICHLORO HEXA-ACETATE

[75] Inventors: Riaz Ahmed Khan, Sonning; Khizar Sultan Mufti, Reading; Kenneth John Parker, Gifford Near Wallingford, all of England

[73] Assignee: Tate & Lyle Limited, London, England

[21] Appl. No.: 639,780

[22] Filed: Dec. 11, 1975

Related U.S. Application Data

[63] Continuation of Ser. No. 514,944, Oct. 15, 1974, abandoned.

[51] Int. Cl.² .............................................. C07H 5/02
[52] U.S. Cl. ........................................ 536/119; 536/122
[58] Field of Search ........... 260/209 R, 234 R, 694 R; 536/119, 122

[56] References Cited

U.S. PATENT DOCUMENTS

| | | | |
|---|---|---|---|
| 2,013,034 | 9/1935 | Cox et al. | 536/119 |
| 2,174,541 | 10/1939 | Walthausen et al. | 536/119 |
| 2,562,883 | 8/1951 | Barham | 536/119 |
| 3,280,103 | 10/1966 | Sinclair | 260/210 R |

OTHER PUBLICATIONS

Evans et al. "Chem. Abst." vol. 68, 1968, p. 87497(t).
Evans et al. "The Jour. of Organic Chem." Mar. 1968, pp. 1074–1076.
Bolton et al. "Carbohydrate Research" 21, 1972 pp. 133–143.
Hough et al "Carbohydrate Research" 25, 1972 pp. 497–503.

*Primary Examiner*—Johnnie R. Brown
*Attorney, Agent, or Firm*—Ostrolenk, Faber, Gerb & Soffen

[57] ABSTRACT

6,6'-Dichloro-6,6'-dideoxysucrose is obtained directly in high yield by reacting sucrose with methanesulphonyl chloride in N,N-dimethylformamide. 1',6,6'-Trichloro-1',6,6'-trideoxysucrose is obtained as a by-product and its formation can be suppressed by starting the reaction at −40° C to −15° C. The dichlorodideoxy and trichloro-trideoxy compounds, which are useful as intermediates for preparing other sucrose derivates, are most conveniently isolated from the reaction mixture in the form of their hexa-acetate and penta-acetate respectively, which are then deacetylated to give the free compounds.

13 Claims, No Drawings

PREPARATION OF SUCROSE 6,6'-DICHLORO HEXA-ACETATE

This is a continuation of application Ser. No. 514,944, filed Oct. 15, 1974, now abandoned.

This invention relates to the preparation of sucrose derivatives.

The sucrose derivatives with which the invention is concerned are compounds having the formula:

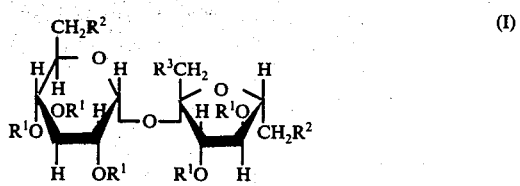

wherein:
(a) $R^1 = $ —H, $R^2 = $ —Cl, $R^3 = $ —OH;
(b) $R^1 = $ —COCH$_3$, $R^2 = $ —Cl, $R^3 = $ —OCOCH$_3$; or
(c) $R^1 = $ —COCH$_3$, $R^2 = $ —Cl, $R^3 = $ —Cl.

The compound of formula (Ia), 6,6'-dichloro-6,6'-dideoxysucrose, is known and is useful as an intermediate in the synthesis of other sucrose derivatives. Heretofore, it has been prepared by the reaction of 6,6'-di-O-tosylsucrose hexa-acetate with benzoyl chloride in pyridine or with sodium chloride in hexamethylphosphoric triamide (by nucleophilic substitution of the tosyloxy groups with chloride ions), or by the reaction of sulphuryl chloride with sucrose or a derivative thereof. However, these two methods produce low yields of the dichloro-dideoxy compound (under 10% and under 30%, respectively), and require chromatographic separation of the product.

It has now surprisingly been discovered that 6,6'-dichloro-6,6'-dideoxysucrose can be obtained directly in high yield by reacting sucrose with methanesulphonyl chloride in N,N-dimethylformamide. Not only is this reaction capable of producing the dichloro-dideoxy compound in much higher yields than the processes used heretofore (e.g. yields of 80% or above), but it also allows the desired product to be recovered easily and, if desired, without resorting to chromatography.

The reaction is suitably performed by slowly adding methanesulphonyl chloride to a cooled solution of sucrose in N,N-dimethylformamide. Preferably, about 10 moles of methanesulphonyl chloride are used per mole of sucrose. It is believed that the reaction proceeds via a methanesulphonyl chloride/N,N-dimethylformamide complex having the formula:

This reaction also yields some 1',6,6'-trichloro-1',6,6'-trideoxysucrose. In order to suppress the formation of this byproduct, it is normally preferred to start the reaction at a temperature of from −40° C. to −15° C., while the methanesulphonyl chloride is being added, and then to complete it by heating the reaction mixture to 60°–70° C. However, if a higher yield of the trichloro-trideoxy compound can be tolerated, the reaction can be performed at higher temperatures, for example initially at about −10° C. and then with heating to about 90° C.

The 6,6'-dichloro-6,6'-dideoxysucrose is most readily isolated in the form of its hexa-acetate - the compound of formula (Ib). This can be formed by adding acetic anhydride to the reaction mixture in pyridine. Concomitantly, any 1',6,6'-trichloro-1',6,6'-trideoxysucrose is converted into its penta-acetate - the compound of formula (Ic). The reaction mixture is suitably maintained at a temperature of from −5° C. to +5° C. during the addition of the acetic anhydride, and then kept at room temperature for about 24 hours. The reaction mixture is then poured into ice-water, and the precipitated acetate is collected and washed. The acetate is de-esterified, suitably with sodium methoxide in methanol at room temperature. The product is de-ionized, concentrated and reacetylated, to free it from any formate by-product which may have been formed during the previous stage. Finally, the hexa-acetate is crystallized and de-acetylated as before, to obtain 6,6'-dichloro-6,6'-dideoxysucrose.

If the reaction of the sucrose with the methanesulphonyl chloride in N,N-dimethylformamide is performed under conditions which yield a relatively high proportion of the trichloride by-product, the 1',6,6'-trichloro-1',6,6'-trideoxysucrose penta-acetate and 6,6'-dichloro-6,6'-dideoxysucrose hexa-acetate obtained after acetylation can be separated from each other by column chromatography on silica gel, using a mixture of ether and light petroleum. The two acetates can then be worked up individually, in the manner already described.

As an alternative to isolation in the form of their acetates (Ib) and (Ic), the dichloro-dideoxy and trichloro-trideoxy derivatives produced by the process of the invention can also be isolated from the reaction mixture by means of column chromatography, although this method is more tedious. The reaction mixture can suitably be chromatographed on a column of silica gel and eluted with a mixture containing approximately equal volumes of methylene chloride and acetone. The trichloro-trideoxy derivative will elute from the column before the dichloro-dideoxy derivative.

The products produced by the process of the invention are valuable as intermediates in the preparation of various known sucrose derivatives, such as the corresponding anhydro, azido and amino derivatives, which can be used, for example, for making resins.

The invention is illustrated by the following Examples.

EXAMPLE 1

Preparation of 6,6'-dichloro-6,6'-dideoxysucrose (a) 6,6'-Dichloro-6,6'-dideoxysucrose hexa-acetate A solution of 20 g of sucrose in 200 ml of N,N-dimethylformamide was treated with 80 ml of methanesulphonyl chloride at −20° C. for 1½ hours. The reaction mixture was brought to room temperature over a period of 2 hours, and then heated at 70° C. for 10 hours.

The reaction mixture was then dissolved in 300 ml of pyridine; and the resulting solution was cooled to −5° C., treated with 40 ml of acetic anhydride, left to stand at room temperature for 6 hours, and then poured into ice-water. The precipitate which formed was washed thoroughly with water and dissolved in methylene chloride. The methylene chloride solution was dried over sodium sulphate and concentrated to a syrup.

The syrupy concentrate was dissolved in dry methanol and treated with sodium methoxide to pH 10. Thin-layer chromatography of the resulting solution on silica gel (Merck 7731; solvent, 8:1 by volume mixture of chloroform and methanol; detection of separated fractions by spraying with 5% solution of concentrated sulphuric acid in methanol and heating at 110°–115° C. for 2–5 minutes) showed a major product which was coincident with an authentic sample of 6,6'-dichloro-6,6'-dideoxysucrose.

The solution obtained after the treatment with sodium methoxide was de-ionized using "Amberlyst 15" catalyst, the catalyst was filtered off, and the filtrate was concentrated to a syrup. The syrupy concentrate was treated with 40 ml of acetic anhydride in 200 ml of pyridine, at room temperature, for 8 hours. The resulting solution was then concentrated by co-distillation with toluene, and the concentrate was crystallized from a mixture of ether and light petroleum, giving 22.4 g of 6,6'-dichloro-6,6'-dideoxysucrose hexa-acetate - the compound of formula (Ib).

Yield: 60.6%.
m.p. = 118°–119° C.
$[\alpha]_D^{25} = +55.8°$ ($c = 1.4$, chloroform).
Reported data: m.p. =117°–118° C.; $[\alpha]_D^{28} = +55°$ ($c = 0.55$, chloroform).
Mass spectrum: m/e = 307.
The i.r. and n.m.r. (100 MHz CDCl$_3$) spectra of the product were identical with those of a standard sample.

(b) 6,6'-dichloro-6,6'-dideoxysucrose

A solution of 10 g of 6,6'-dichloro-6,6'-dideoxysucrose hexa-acetate in 200 ml of anhydrous methanol was treated with sodium methoxide to pH 10, at room temperature, for 24 hours. The resulting solution was de-ionized with "Amberlyst 15" catalyst, filtered and concentrated, giving 5.8 g of 6,6'-dichloro-6,6'-dideoxysucrose as a syrup - the compound of formula (Ia).

Yield: 98%.
$[\alpha]_D^{25} = +60.5°$ ($c = 0.91$, water).
Reported data: $[\alpha]_D^{25} = +60°$ ($c = 0.52$, water).

EXAMPLE 2

Preparation of 1',6,6'-trichloro-1',6,6'-trideoxysucrose and 6,6'-dichloro-6,6'-dideoxysucrose (a) 1',6,6'-Trichloro-1',6,6'-trideoxysucrose penta-acetate A solution of 10 g of sucrose in 200 ml of N,N-dimethylformamide was treated with 80 ml of methanesulphonyl chloride at −10° C. for 1½ hours. The reaction mixture was brought to room temperature, and then heated with stirring at 85° C. for 24 hours.

The resulting reaction mixture was worked up as in Example 1 (a), giving a mixture of acetylated products. This mixture was separated by chromatography on a column of silica gel (Merck "Silica gel 60," 70–230 mesh ASTM) eluted with a 1:1 by volume mixture of ether and light petroleum. The chromatographic separation gave first 3.54 g of 1',6,6'-trichloro-1',6,6'-trideoxysucrose penta-acetate as a syrup — the compound of formula (Ic).

Yield: 20%.
$[\alpha]_D^{25} = +61.0°$ ($c = 1.04$, chloroform).
Mass spectrum: m/e = 307 (hexopyranosyl cation) and 283 (ketofuranosyl cation).
N.m.r. (100 MHz, CDCl$_3$):
τ4.3 (d, J$_{1,2}$ 3.7 Hz, H-1);
5.1 (q, J$_{2,3}$ 10.0 Hz, H-2);
4.57 (t, J$_{3,4}$ 10.0 Hz, H-3);
4.92 (t, J$_{4,5}$ 10.0 Hz, H-4);
4.33 (d, J$_{3',4'}$ 6.0 Hz, H-3');
7.8–9.03 (m, 5 -COCH$_3$).

(b) 1',6,6'-Trichloro-1',6,6'-trideoxysucrose

The 1',6,6'-trichloro-1',6,6'-trideoxysucrose penta-acetate obtained in part (a) above, was de-esterified with sodium methoxide in methanol, by the same procedure as used in Example 1 (b), giving 1',6,6'-trichloro-1',6,6'-trideoxysucrose. The product was identified by treating it with benzoyl chloride in pyridine, giving the known 1',6,6'-trichloro-1',6,6'-trideoxysucrose pentabenzoate, the physical constants, i.r. spectrum and n.m.r. spectrum of which were identical with those of a standard sample.

(c) 6,6'-Dichloro-6,6'-dideoxysucrose

Continuing the elution of the silica gel column in part (a) above yielded a fraction containing 6,6'-dichloro-6,6'-dideoxysucrose hexa-acetate — the compound of formula (Ib). This fraction was collected, concentrated and crystallized from a mixture of ether and light petroleum, to give 9.22 g of the hexa-acetate (50% yield). The hexa-acetate was de-acetylated by the same procedure as in Example 1 (b), to give 6,6'-dichloro-6,6'-dideoxysucrose — the compound of formula (Ia). The products had the same constants as those of Example 1.

We claim:

1. A process for preparing a sucrose derivative, which comprises reacting a cooled solution of sucrose in N,N-dimethylformamide with methanesulphonyl chloride, contacting the resulting product in situ with an acetylating agent whereby the hexa-acetate of 6,6'-dichloro-6,6'-dideoxysucrose is formed, and isolating said hexa-acetate from the reaction mixture.

2. The process according to claim 1, wherein the methanesulphonyl chloride is added to a solution of the sucrose in N,N-dimethylformamide at a temperature of from about −40° C. to about −15° C., and the resulting reaction mixture is then heated to a temperature of about 60°–70° C. in order to complete the reaction.

3. The process according to claim 1, wherein about 10 moles of methanesulphonyl chloride are used per mole of sucrose.

4. The process according to claim 1 wherein said hexa-acetate is deacetylated by contact with a deacetylating agent to give free 6,6'-dichloro-6,6'-dideoxysucrose.

5. A process for producing sucrose derivatives, which comprises reacting a cooled solution of sucrose in N,N-dimethylformamide with methanesulphonyl chloride, contacting the resulting product in situ with an acetylating agent whereby the hexa-acetate of 6,6'-dichloro-6,6'-dideoxysucrose and the penta-acetate of 1',6,6'-trichloro-1',6,6'-trideoxysucrose are formed, and isolating the hexa-acetate and penta-acetate from the the reaction mixture.

6. The process according to claim 5, wherein about 10 moles of methanesulphonyl chloride are used per mole of sucrose.

7. The process according to claim 5 wherein said hexa-acetate and said penta-acetate are deacetylated by contact with a deacetylating agent to give free 6,6'-dichloro-6,6'-dideoxysucrose and 1',6,6'-trichloro-1',6,6'-trideoxysucrose, respectively.

8. The process according to claim 7, wherein the said hexa-acetate and penta-acetate are separated from each other by means of column chromatography.

9. The process according to claim 2 wherein about 10 moles of methanesulphonyl chloride are used per mole of sucrose, and wherein said hexa-acetate is deacetylated by contact with a deacetylating agent to give free 6,6'-dichloro-6,6'-dideoxysucrose.

10. The process according to claim 6 wherein the methanesulphonyl chloride is added to the solution of the sucrose at a temperature from about −40° C. to about −15° C., and the resulting mixture is then heated to a temperature of about 60° to 70° C. in order to complete the reaction.

11. The process according to claiam 10 wherein said hexa-acetate and penta-acetate are deacetylated by contact with a deacetylating agent to give free 6,6'-dichloro-6,6'-dideoxysucrose and 1',6,6'-trichloro-1',6,6'-trideoxysucrose, respectively.

12. The process according to claim 4 wherein said deacetylated free 6,6'-dichloro-6,6'-dideoxysucrose is re-acetylated by contact with an acetylating agent and the re-acetylated product is deacetylated by contact with a deacetylating agent to give free 6,6'-dichloro-6,6'-dideoxysucrose.

13. The process according to claim 7 wherein said deacetylated free 6,6'-dichloro-6,6'-dideoxysucrose and 1',6,6'-trichloro-1',6,6'-trideoxysucrose is re-acetylated by contact with an acetylating agent and the re-acetylated product is deacetylated by contact with a deacetylating agent to give free 6,6'-dichloro-6,6'-dideoxysucrose and 1',6,6'-trichloro-1',6,6'-trideoxysucrose.

* * * * *